United States Patent [19]

Lawrenson

[11] Patent Number: 4,556,741

[45] Date of Patent: Dec. 3, 1985

[54] DISMUTATION OF FUNCTIONALIZED OLEFINS

[75] Inventor: Malcolm J. Lawrenson, Swanland, England

[73] Assignee: BP Chemicals Limited, London, England

[21] Appl. No.: 555,390

[22] Filed: Nov. 28, 1983

[30] Foreign Application Priority Data

Dec. 2, 1982 [GB] United Kingdom ............. 8234383

[51] Int. Cl.⁴ ............................................. C07C 45/45
[52] U.S. Cl. .................................... 568/395; 560/190; 570/237; 568/673
[58] Field of Search ................ 568/395, 673; 560/190; 570/237

[56] References Cited

U.S. PATENT DOCUMENTS 3,974,196  8/1976  Nakamura et al. ............... 568/388
3,974,233  8/1976  Lawrenson ........................ 568/647
4,269,780  5/1981  Banasiak ........................... 560/231
4,454,368  6/1984  Banks ................................ 585/646

OTHER PUBLICATIONS

Mol, Chem. Tech., pp. 250–255, (1983).

*Primary Examiner*—James H. Reamer
*Attorney, Agent, or Firm*—Brooks, Haidt, Haffner & Delahunty

[57] ABSTRACT

This invention relates to a process for dismuting functionalized olefins using a catalyst which has rhenium heptoxide on phosphated alumina and a metal hydrocarbon compound such as an alkyl tin. The olefins that may be dismuted are those which have a hetero atom such as oxygen, nitrogen or halide in the chain. Specific examples are olefinic compounds which have an ester, ether or a ketone group. The products of the reaction are useful chemical intermediates.

7 Claims, No Drawings

DISMUTATION OF FUNCTIONALIZED OLEFINS

The present invention relates to the dismutation of functionalised olefins.

Functionalised olefins are olefinically unsaturated compounds containing one or more heteroatoms eg unsaturated halides, esters, nitriles or ethers.

Dismutation is a reaction in which an interchange of alkylidene moieties between olefins occurs, viz: reacting $R-CH=CH-R^1$ with $R^2-CH=CH-R^3$ to form $R-CH=CH-R^2$ and $R^1-CH=CH-R^3$, ie to give different olefinically unsaturated compounds. The reaction may be self-dismutation in which two molecules of the same compound split and recombine to give two molecules of different compounds, or the reaction may be co-dismutation in which the two initial molecules, which split and recombine to give two other olefinic compounds, are different. In the case of functionalised olefins, at least one of the groups $R, R^1, R^2, R^3$ contains the heteroatom.

Such dismutation metathesis (or disproportionation) reactions are well known for hydrocarbons containing no heteroatoms. For instance U.S. Pat. No. 3974233 discloses that olefinic hydrocarbons can be dispropor-tionated over a rhenium heptoxide/alumina catalyst.

It is also known eg from JCS Chem. Comm. 1221 (1972) that dismutation reactions can be carried out using functionalised olefinic compounds as defined above. However, whilst a wide variety of metallic compounds are effective catalysts in the absence of heteroatoms, the number of catalysts that are not affected by the heteroatom in the dismutation of functionalised olefins is small. Catalysts which can be used satisfactorily with olefinic hydrocarbons often do not work with functionalised olefins or do not give satisfactory yields.

It is an object of the invention to dismute functionalised olefins.

Accordingly, the present invention is a process for the catalytic dismutation of a functionalised olefin comprising bringing the functionalised olefin into contact with a rhenium heptoxide/phosphated alumina catalyst and a metal hydrocarbon compound.

The heteroatom in the functionalised olefin may be an atom of oxygen or nitrogen or a halide. It is preferably a non-hydroxylic oxygen atom eg an ester, ether or ketone.

The reaction can be carried out using compounds containing more than one olefinic double bond but the mixture of products obtained will generally be excessively complex. It is therefore preferred to use compounds containing a single olefinic double bond.

The functionalised olefin used in the process of the present invention may for example have from 2 to 30 carbon atoms in the molecule.

The olefinic double bond may for example be a terminal double bond $(CH_2=)$ or may be internal $(R-CH=)$, where R is hydrocarbyl, eg alkyl, preferably methyl. The preferred functionalised olefin structures are of the form $R-CH=CH-(CH_2)_n-X$, where R is a H atom or an alkyl group, X is the functional group containing the heteroatom and n has a value of 1 or more. R is preferably a H atom.

Using the process of the present invention, a functionalised olefin may also be dismuted with another functionalised olefin or with an unfunctionalised olefin.

Methods of producing phosphated rhenium heptoxide/alumina catalysts are described in U.S. Pat. No. 3974233 and GB 1216587. For instance, they may be prepared by impregnating alumina with phosphate ions prior to depositing the rhenium as disclosed in GB 1216587. They may also be prepared by treating the alumina support by a digestion technique (hereafter referred to as 'digestion') with an aqueous solution of an ammonium phosphate, followed by separation of the treated alumina and deposition of rhenium e.g. by impregnation with ammonium perrhenate and calcination to give rhenium heptoxide.

Digestion involves steeping the support in a solution of the salt and thereafter removing both excess solvent and solute eg by washing. At no point is the support allowed to become dry or uncovered so that it is always in equilibrium with the excess of external solution. It is believed that digestion allows only preferential incorporation of the solute on to specific sites within the carrier and is therefore more selective than impregnation.

The term "an ammonium phosphate" used throughout this specification is intended to include ammonium phosphate itself, ammonium dihydrogen phosphate and diammonium hydrogen phosphate. Of these diammonium hydrogen phosphate is preferred.

The preferred alumina is gamma-alumina derived from boehmite prepared by the hydrolysis of aluminium alkoxides resulting from oxidation of the products of a Ziegler-type reaction of a lower molecular weight aluminium alkyl and an alpha mono-olefin.

Rhenium heptoxide may be loaded on to the modified support by any known method. Suitable examples of such methods include those described in our U.S. Pat. Nos. 3424312 and 3448163, though it is preferred to impregnate the modified support with an aqueous solution of rhenium heptoxide or a compound of rhenium capable of forming rhenium heptoxide followed by drying. Suitable rhenium compounds capable of being decomposed by heat to rhenium heptoxide include ammonium perrhenate and perrhenic acid.

Sufficient amounts of an ammonium phosphate may be employed in the digestion to result in an alumina containing between 1 and 16%, preferably 2 to 10% of phosphate ion.

Digestion is suitably effected at temperatures between ambient and the boiling point of the aqueous ammonium phosphate solution, preferably at temperatures between 40° C. and the boiling point. Elevated pressure may be used but digestion at atmospheric pressure is preferred.

In a modification of the process for the production of the catalyst the alumina may be digested with an aqueous solution of aluminium nitrate prior to digestion with the aqueous ammonium phosphate solution. However, this aluminium nitrate step is unnecessary for the boehmite type of alumina prepared by the hydrolysis of aluminium alkoxides.

The period of digestion with aqueous ammonium phosphate depends on a number of factors including the temperature, the concentration of the ammonium phosphate solution and the degree of addition of phosphate ion required. Digestion is suitably continued for a period of 0.5 to 24 hours, preferably 1 to 12 hours and even more preferably 1 to 6 hours.

After digestion, the treated alumina may be separated from the digestant by sieving. It is preferred to wash, dry and calcine the alumina prior to loading with rhenium heptoxide.

The catalyst may contain 1 to 15 percent by weight rhenium heptoxide, preferably 1 to 12 percent and even more preferably 1 to 6 percent.

In addition to the phosphated rhenium heptoxide/alumina catalyst, a metal hydrocarbon compound i.e. a co-catalyst is also required.

This co-catalyst is preferably selected from a monohydrotrialkyl-, a tetraalkyl-, a monohydrotriaryl- and a tetraaryl-derivative of the metal. The metal atom in the metal hydrocarbon compound is suitably selected from those in Groups IIB, IIIA and IVA of the Periodic Table of Elements in the 44th Edition of the "Handbook of Chemistry and Physics", Ed. Hodgman, C. D. et al, pp 448 and 449 (1963) and published by The Chemical Rubber Publishing Co., Ohio, U.S.A. The metal is preferably selected from zinc, mercury, aluminium, tin, germanium and lead. The metal hydrocarbon compound is most preferably tetra-methyl-tin.

The dismutation reaction may be carried out over a wide range of conditions. The reaction temperature may for example be from $-20°$ C. to $200°$ C. preferably $10°$ C. to $100°$ C.

The pressure is not critical and the process may be carried out at atmospheric pressure or at elevated or reduced pressures.

The reaction is conveniently carried out by passing the functionalised olefin over a bed of the phosphated rhenium heptoxide/alumina catalyst that has been pretreated with the co-catalyst. Alternatively, the co-catalyst may be continually supplied with the olefinic feed. The contact time may for example, be in the range 5 mins. to 1 hour.

The invention will now be illustrated by reference to the following Examples.

EXAMPLES

A. Catalyst Preparation (1) A catalyst containing 6.5% wt/wt rhenium heptoxide and 2.76% wt/wt phosphate was prepared for use in the process of the present invention as follows:

100 g of gamma-alumina extrudate was saturated with 120 ml of distilled water. To this, was added a solution of 6.2 g diammonium hydrogenphosphate in 120 ml of water and the mixture was stirred for 4 h at $50°$ C. The excess liquid was filtered off and the filtrate washed with water and dried at $100°$ C. for 16 h, (phosphated base).

2.38 g of ammonium perrhenate in 30 ml of water was impregnated onto 30 g of the phosphated base in 10 ml aliquots. The water was removed after each addition on a rotary evaporator. The catalyst was then heat treated in air at $550°$ C. per 6 h and further activated for 3 h at $450°$ C. in air immediately before use.

(2) A catalyst containing 6.05 wt/wt rhenium heptoxide and 3.1% wt/wt phosphate was prepared as described above by impregnation of 34.1 g of phosphated alumina by a solution of 2.75 g of ammonium perrhenate in 35 ml of water. This was then heat treated in air at $550°$ C. for 6 h and activated at $550°$ C. in air for 18 h before use.

B. EXAMPLE 1

3 g of the catalyst prepared as in A(1) was placed in a batch reactor and a solution of 10 microliters of tetramethyltin in 5 ml of toluene were added. 3 ml of hex-5-en-2-one were then added. The ethylene produced was allowed to vent off and after a day the conversion to dec-5-en-2,9-dione was found to be 26%.

EXAMPLES 2 AND 3

In each case, 4 g of the catalyst prepared as in A(2) were placed in a continuous fixed bed reactor and pretreated with a solution of 30 microliters of tetramethyltin in 7 ml of n-heptane. Solutions of 10 ml each of (a) methyl pent-4-enoate and (b) allyl chloride per 35 ml of n-heptane were prepared and each was passed over the treated catalysts at a rate of 12 ml/hour.

In the case of methyl pent-4-enoate, a maximum conversion of 48% to the $C_8$ diester was achieved. For allyl chloride a maximum conversion of 53% to 1,4-dichlorobutene-2 was obtained.

I claim:

1. A process for the catalytic dismutation of a functionalized olefin having a heteroatom which is a non-hydroxylic oxygen atom selected from the group consisting of an ester, ether or a ketone, which process comprises bringing the functionalized olefin into contact with a catalyst which comprises
   (a) a rhenium heptoxide component,
   (b) a phosphated alumina component obtained by treating alumina with a source of phosphate, and
   (c) a metal hydrocarbon compound component selected from the group consisting of a mono-hydrotrialkyl-, a tetroalkyl-, a monohydrotriaryl-, and a tetraaryl- derivative of zinc, mercury, aluminum, tin, germanium or lead.

2. A process according to claim 1 wherein the reaction is carried out with functionalised olefin compounds containing a single olefinic double bond.

3. A process according to claim 2 wherein the functionalised olefin has from 2 to 30 carbon atoms in the molecule.

4. A process according to claim 1 wherein the functionalised olefin structure is of the form $R-CH=CH-(CH_2)_n-X$, where R is a H atom or an alkyl group, X is the functional group containing the heteroatom and n has a value of 1 or more.

5. A process according to claim 1 wherein the metal hydrocarbon compound is tetra-methyl tin.

6. A process according to claim 1 wherein the dismutation reaction is carried out at a temperature from $-20°$ C. to $200°$ C.

7. A process according to claim 1 wherein the reaction is carried out either by passing the functionalised olefin over a bed of the phosphated rhenium heptoxide/alumina catalyst that has been pretreated with the metal hydrocarbon compound, or the metal hydrocarbon compound is continually supplied to the reactor along with the functionalised olefinic feed.

* * * * *